United States Patent
DiBiasi

(10) Patent No.: US 10,398,828 B2
(45) Date of Patent: Sep. 3, 2019

(54) TAMPER-EVIDENT PEN NEEDLE OUTER COVER

(71) Applicant: Becton, Dickinson and Company, Franklin Lakes, NJ (US)

(72) Inventor: Michael DiBiasi, West Milford, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 160 days.

(21) Appl. No.: 15/317,461

(22) PCT Filed: Jun. 8, 2015

(86) PCT No.: PCT/US2015/034700
§ 371 (c)(1),
(2) Date: Dec. 9, 2016

(87) PCT Pub. No.: WO2015/191457
PCT Pub. Date: Dec. 17, 2015

(65) Prior Publication Data
US 2017/0106136 A1   Apr. 20, 2017

Related U.S. Application Data

(60) Provisional application No. 62/009,475, filed on Jun. 9, 2014.

(51) Int. Cl.
*B65D 83/10* (2006.01)
*A61M 5/00* (2006.01)
(Continued)

(52) U.S. Cl.
CPC .......... *A61M 5/002* (2013.01); *A61M 5/50* (2013.01); *B65D 43/16* (2013.01); *B65D 43/22* (2013.01);
(Continued)

(58) Field of Classification Search
CPC .............. B65D 43/16; B65D 43/22; B65D 2101/0023; B65D 2543/00833;
(Continued)

(56) References Cited

U.S. PATENT DOCUMENTS 4,623,336 A * 11/1986 Pedicano .............. A61M 5/002
604/110
4,784,296 A   11/1988 Bullock
(Continued)

FOREIGN PATENT DOCUMENTS

| JP | 2001286562 | 10/2001 |
| JP | 2012517282 | 8/2012 |
| WO | WO-2010090735 A1 | 8/2010 |

*Primary Examiner* — Luan K Bui
(74) *Attorney, Agent, or Firm* — Dickinson Wright PLLC

(57) ABSTRACT

A pen needle outer cover (10) has a molded plastic distal cover (20), and a molded plastic proximal cover (22) in place of the conventional paper-foil label. The proximal cover (22) may be snap-fit over the opening of the distal cover (20). A user-separable section (26) with a finger pull tab (32) is defined by a reduced-thickness membrane (24), which functions as a tear line to allow that section (26) to at least partially separate from the proximal cover (22). A living hinge (27) may be provided to keep the user-separable section (26) from completely separating from the proximal cover (22). The finger pull tab (32) may be configured to enable re-covering of a pen needle (30) that is still within the outer cover (10).

17 Claims, 4 Drawing Sheets

(51) Int. Cl.
- *A61M 5/50* (2006.01)
- *B65D 43/16* (2006.01)
- *B65D 43/22* (2006.01)
- *A61M 5/32* (2006.01)

(52) U.S. Cl.
CPC ....... *A61M 5/3205* (2013.01); *A61M 2205/60* (2013.01); *B65D 2101/0023* (2013.01); *B65D 2543/00833* (2013.01)

(58) Field of Classification Search
CPC ...... A61M 5/002; A61M 5/50; A61M 5/3202; A61M 5/3205; A61M 5/3213; A61M 2205/60
USPC .......... 206/365, 438; 604/110, 111, 192, 263
See application file for complete search history.

(56) References Cited

U.S. PATENT DOCUMENTS

| | | | |
|---|---|---|---|
| 5,968,021 A * | 10/1999 | Ejlersen | A61M 5/3213 206/365 |
| 5,971,966 A * | 10/1999 | Lav | A61M 5/002 206/365 |
| 2002/0104843 A1 | 8/2002 | Smith et al. | |
| 2006/0032769 A1* | 2/2006 | Erickson | A61M 5/002 206/365 |
| 2008/0097342 A1 | 4/2008 | Gordin | |
| 2009/0069752 A1 | 3/2009 | Raj et al. | |
| 2011/0071471 A1* | 3/2011 | Dibiasi | A61M 5/3202 604/111 |
| 2012/0016300 A1 | 1/2012 | Ruan | |
| 2012/0029440 A1 | 2/2012 | Boyd et al. | |

* cited by examiner

TAMPER-EVIDENT PEN NEEDLE OUTER COVER

CROSS-REFERENCE TO RELATED APPLICATION

This application claims priority to U.S. provisional patent application No. 62/009,475, filed Jun. 9, 2014, which is incorporated herein by reference in its entirety.

FIELD OF THE INVENTION

This invention relates to packaging for individual pen needles that are adapted for attachment to a medication delivery device, such as a medication pen, and specifically to a closure for a pen needle distal outer cover.

BACKGROUND OF THE INVENTION

Pen needles are designed to be attached to a medication pen and are especially useful for delivering self-administered injectable medications, such as insulin. Medication pens and associated pen needles are disclosed in U.S. Pat. No. 7,645,264, and in U.S. Patent Application Publication Nos. 2009/0069755 and 2012/0022460, all of which are incorporated herein by reference in their entirety for their teachings of pen needle design and construction.

In one well-known commercial pen needle device, a needle-bearing hub is provided inside a funnel-shaped, outer plastic cover. The needle (cannula) is affixed in an axial bore of the hub with one end (the "injection end") protruding from the distal or "patient side" of the hub and covered by a removable inner cover, and the other end (the "non-injection end") recessed in a cavity on the proximal or "non-patient" side of the hub, which is adapted for attachment to a medication pen. The hub and the injection end are received in the outer cover, where the hub is secured in position by ribs, and a closure in the form of a paper and foil "teardrop" label is heat-sealed on the edge or flange of the open end of the cover. The user removes the label and holds the outer cover to install the hub, typically threading the hub onto the medication pen. Once the hub is installed on the pen, the outer cover can be removed by pulling it distally off the hub. The inner cover is then removed from the injection end of the needle to allow an injection to be made.

Current pen needle labels have a plastic layer on the underside and are fastened to the flange of a pen needle outer cover using heat to melt the plastic layer to the plastic flange. The heating and its associated dwell time are critical, and must be maintained through hundreds of thousands of sealing repetitions per day. In large-scale pen needle manufacturing, this heat seal step may become a bottleneck or rate-limiting step. Therefore, one object of the invention is to provide a closure for a pen needle outer cover that does not require a heat-sealing step to attach it to the outer cover, while retaining all the sterility and ease-of-use functionality of current products.

Current pen needle labels may also be subject to delamination in some regions and under certain conditions where the labels are exposed to high levels of humidity, or if the packaging gets wet. Delamination can render the pen needle unusable by leaving the plastic bottom layer of the label intact across the outer cover opening while the outer layers of the label delaminate when the patient tries to remove the label to access the needle. Therefore, another object of the invention is to avoid the drawbacks associated with delamination of a peel-type label for a pen needle.

A further problem addressed by the invention relates to providing evidence of tampering when a pen needle has been opened. Current pen needle labels can be reattached to the outer cover flange by reheating the plastic underlayer of the label and pressing it against the outer cover flange, or by using adhesives. The pen needle label can be made to look as though it is intact even though the sterility barrier has been compromised. Thus, another object of the invention is to provide a tamper-evident closure and labeling system.

Current pen needle labels are generally peeled completely off the outer cover flange, which leaves the user with a loose piece to discard. Some pen needle users peel the label off only partially along its sealed area, leaving a small portion of the label attached to the outer cover flange. This pattern of use makes it difficult to install the pen needle on a medication pen, as it requires the pen to be inserted into the pen needle cover at an angle to access the needle-bearing hub while avoiding the hanging label, which could get caught between the threads of the medication pen and the needle hub. Thus, another object of the invention is to provide a pen needle closure that allows the user to leave a user-separable portion of the closure attached to the outer cover while leaving an unobstructed opening for installation of the pen-needle on a medication pen.

SUMMARY OF THE INVENTION

These and other objects of the invention are achieved, in one aspect, with a pen needle outer cover, comprising: a plastic distal cover portion having a closed distal end and an opening at a proximal end with an attachment member adjacent the opening; and a plastic proximal cover portion engaging the attachment member and having a rupturable, thin-walled border portion defining a user-separable section of the proximal cover portion.

In embodiments, the user-separable section remains attached to the proximal cover portion by a living hinge after the pen needle is opened. In embodiments without a living hinge, the user-separable section can be removed completely from the outer cover portion. The user-separable section may have a finger pull tab at its outer end to facilitate rupture of the thin-walled body portion.

In embodiments, the distal cover portion includes a first latching portion, while the proximal cover portion includes a second latching portion configured to engage the first latching portion. The latching portions can be incorporated, respectively, on a sidewall of the distal cover portion and on a finger pull tab of the user-separable section. In embodiments, the latching portions can be releasably re-engaged to re-cover an opened pen needle.

In embodiments, the proximal cover portion is transparent, which enables viewing of mating portions of the distal cover portion.

BRIEF DESCRIPTION OF THE DRAWINGS

Embodiments of the disclosed invention are described in detail below only by way of example and with reference to the accompanying drawing figures, which are not necessarily to scale.

DETAILED DESCRIPTION OF EMBODIMENTS OF THE INVENTION

As used herein, the "distal" direction is in the direction of the injection site, and the "proximal direction" is the opposite direction. The "axial" direction is along the longitudinal axis of the cannula. The cannula is generally arranged axially in the device. "Radially" is a direction perpendicular to the axial direction; thus, "radially inward" generally means closer to the needle.

Figure 1:
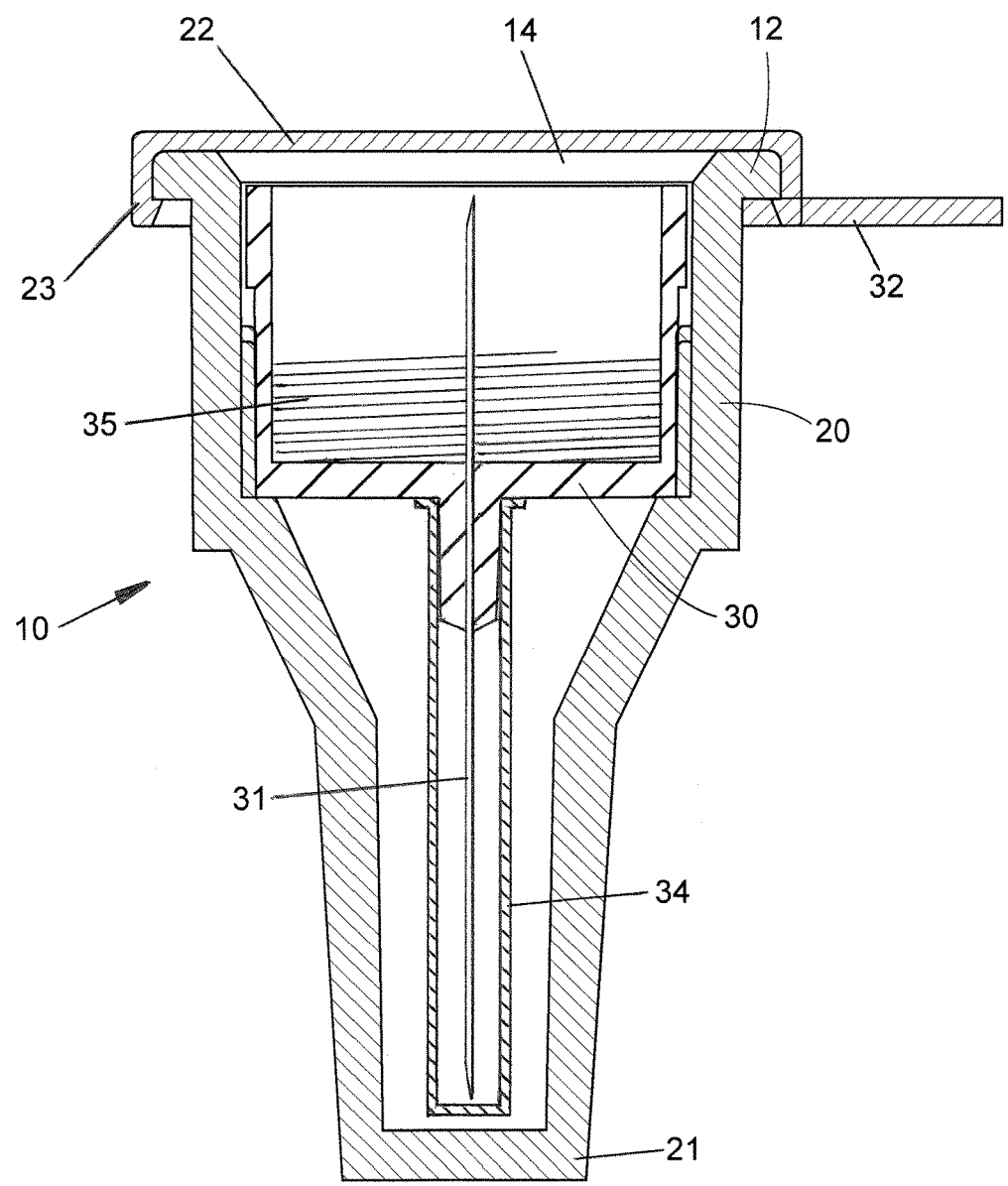
FIG. 1 is a schematic, longitudinal cross-sectional view of a pen needle outer cover that shows certain basic features common to various embodiments of the invention.

Referring to FIG. 1, a pen needle outer cover 10 according to the invention generally comprises a distal cover 20 and a proximal cover 22, both of which are injection molded parts made of plastic. In the illustrated embodiments, the distal cover 20 is a conventional funnel-shaped, substantially rigid pen needle outer cover that has an open proximal end 14 and narrows in the distal direction to a closed end 21. A commercial pen needle is installed in distal cover 20 through the open proximal end 14. The pen needle has a needle 31 fixed in a needle-bearing hub 30. The injection end of needle 31 is sheathed in a removable inner cover 34. Threads 35 on the inside of hub 30 are configured to mate with the threads of a medication pen.

An attachment member in the form of an integral, outwardly directed flange 12 extends around substantially the entire open proximal end 14. In other embodiments, an attachment member on the distal cover 20 may face inward at the edge of its proximal opening 14 and engage a mating member on proximal cover 22. Other means for mounting proximal cover 22 to the proximal end of distal cover 20 are also within the scope of the invention.

Figure 2:
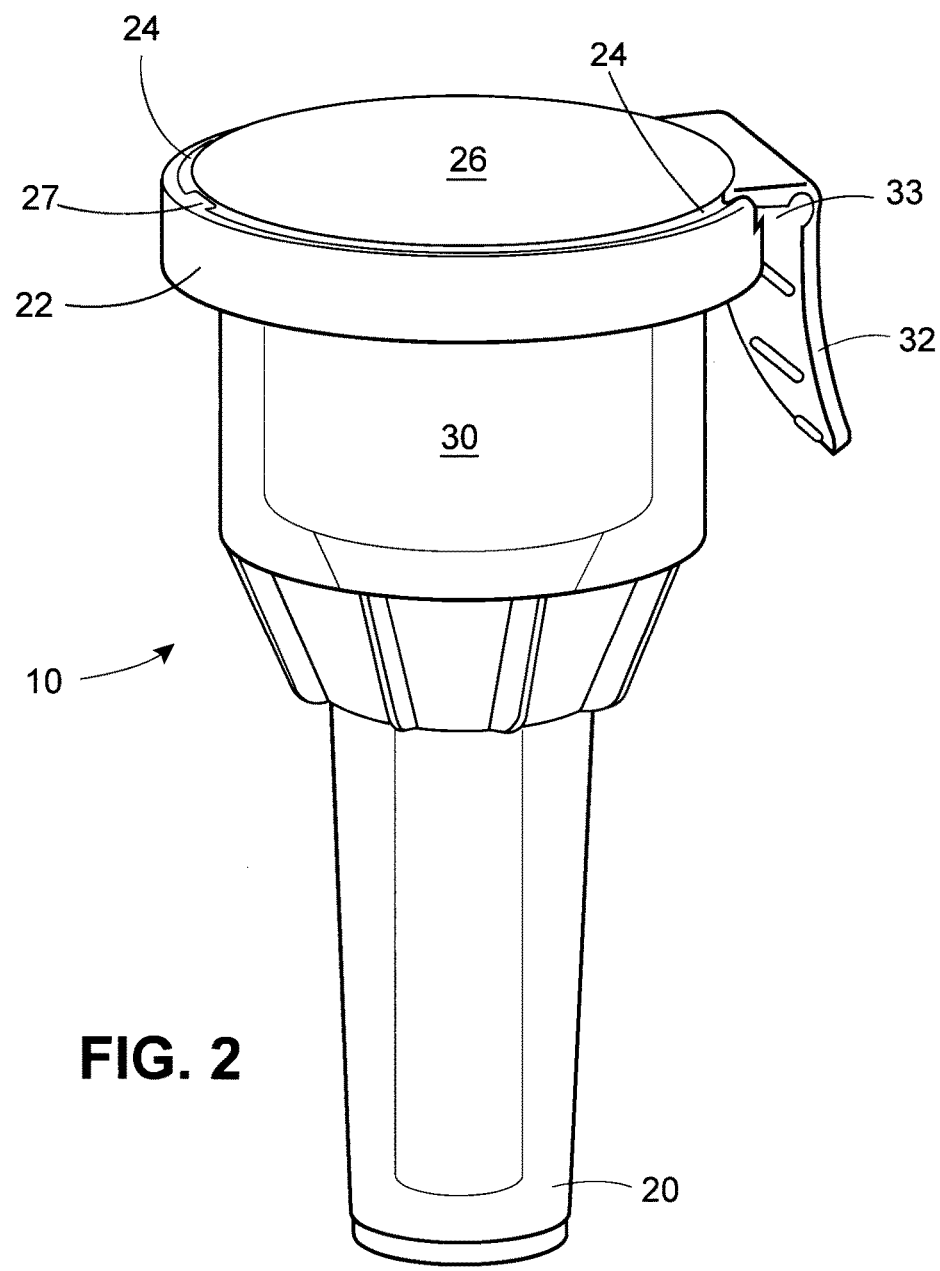
FIG. 2 is a perspective view of a pen needle outer cover according to another embodiment of the invention.
Figure 3:
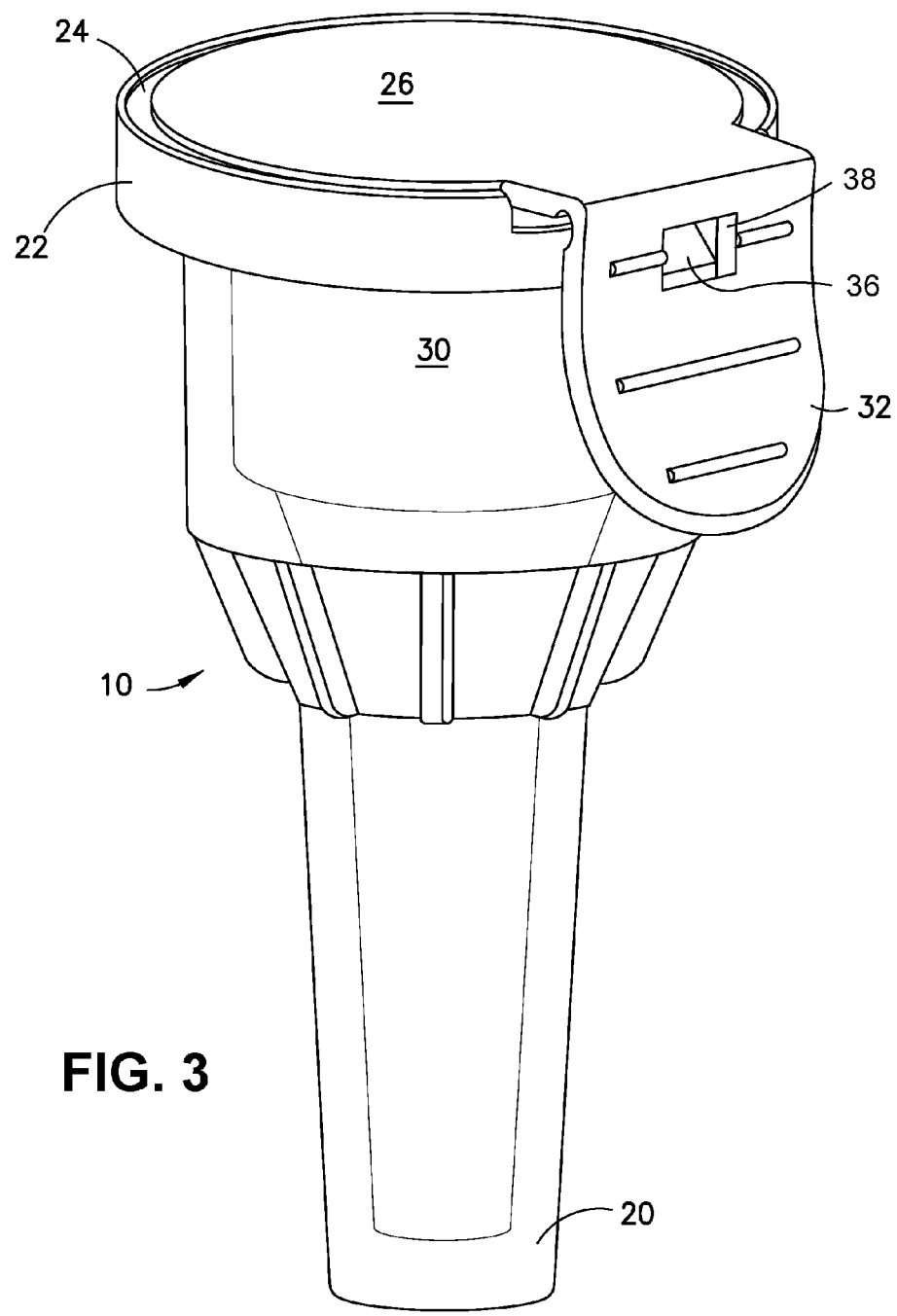
FIG. 3 is another perspective view thereof.
Figure 4:
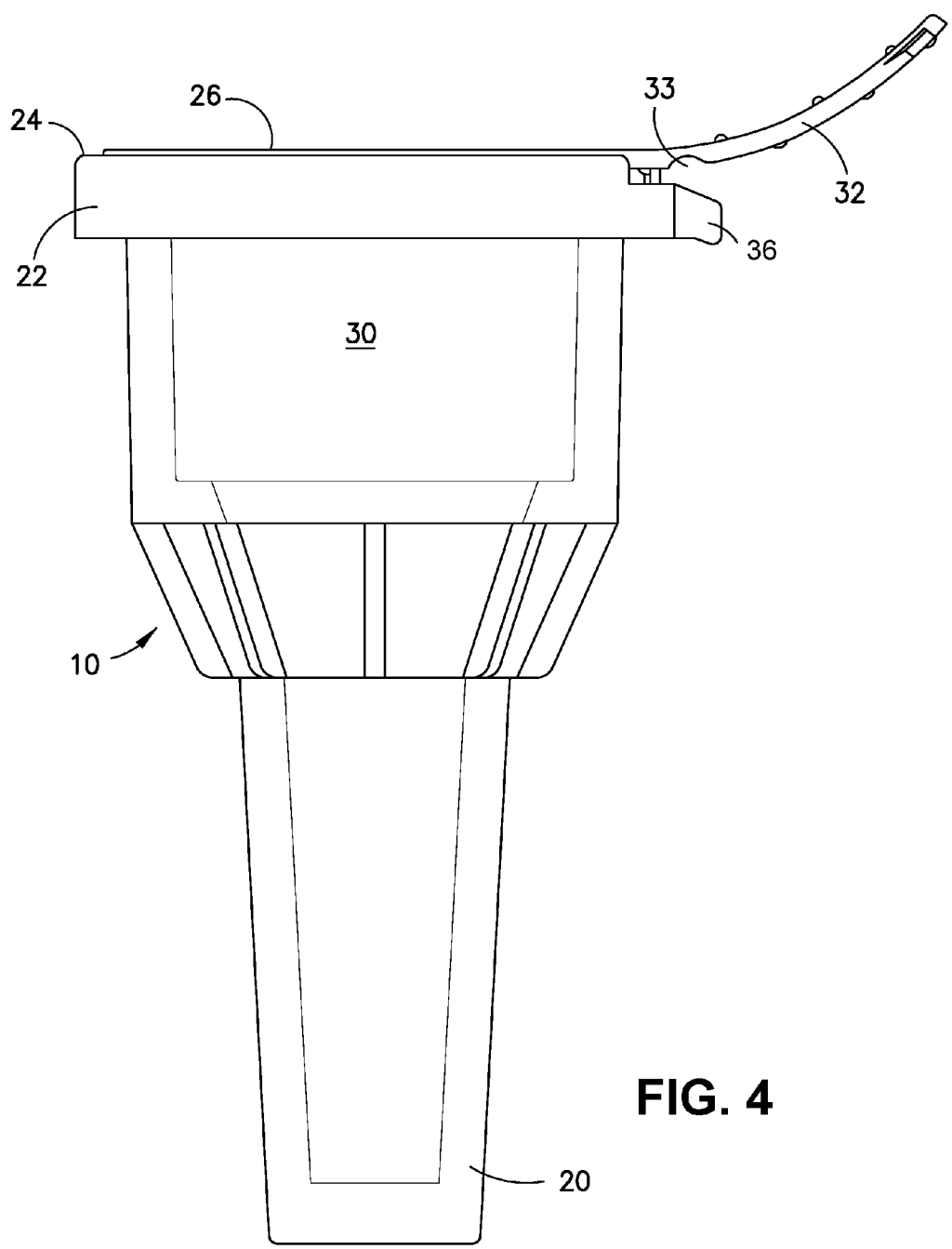
FIG. 4 is an elevational view thereof.

As shown in FIG. 1, the proximal cover 22 of the invention is configured with a flexible, resilient, undercut skirt 23 to snap-fit over the flange 12 of distal cover 20. The embodiment of FIGS. 2-4 and others preferably have such a skirt or a similar snap-fit arrangement. In embodiments, the attachment may be further secured by heat-shrinking an additional membrane of cellophane or the like around the outer cover, or an adhesive may be applied to the underside of proximal cover 22. Other outer cover shapes could also be employed within the scope of the invention. Proximal cover 22 preferably is made of polyethylene, although polypropylene or other plastics known in the art and used in this field may be used in other embodiments. The material may be opaque but preferably is translucent, and more preferably is transparent so that the interior of the outer cover can be viewed easily from the outside. Proximal cover 22 is more rigid than the conventional paper and foil "teardrop" labels that it replaces. Except for its flexible and/or rupturable portions described below, proximal cover 22 may be semi-rigid or substantially rigid.

While the two cover portions 20, 22 may be completely separable, it is preferred that they remain at least partially attached to each other at all times. Thus, in the embodiment illustrated in FIGS. 2-4, only a central user-separable section 26 of proximal cover 22 can be pulled back to provide access to the needle-bearing hub inside. In this case, a rupturable, thin-walled border portion or membrane 24 functions as a tear line and thus defines the user-separable section 26. The thickness of this thin-walled membrane 24 may be selected by persons skilled in the art to achieve the appropriate tear strength, depending on the cover material(s) used. In embodiments, a thickness of 0.004 to 0.012 mm, and preferably 0.004 mm, for the thin-walled portion was found to provide an acceptable tear strength for the preferred injection molded polyethylene material.

If the thin-walled membrane 24 is continuous—i.e., if it extends uninterrupted from one part of the proximal cover's outer edge to another part of the outer edge, thus defining a closed shape—the user-separable section 26 can be completely removed, leaving the remainder of proximal cover 22 intact on distal cover 20. Alternatively and preferably, a living hinge 27 (see FIG. 2) on the proximal cover 22 interrupts the thin-walled border portion 24. Living hinge 27 keeps the user-separable section 26 partially attached to cover 22 when the user-separable section is separated at the thin-walled border portion 24. In the illustrated, preferred symmetrical arrangement, the living hinge 27 divides the thin-walled border portion 24 into two equal-length segments. The living hinge is a piece of plastic, co-molded with the proximal cover 22, that bends without breaking to allow the user-separable section 26 to pivot open and provide unobstructed access to the needle-bearing hub 30 through the opening at the proximal end 14 of distal cover 20. Living hinge 27 is thinner than the majority of proximal cover 22 but thicker than the thin-walled border portion 24. Details of the thickness and width of the living hinge may be left to the discretion of persons skilled in the art, depending on the geometry of the proximal cover and the material used.

In embodiments, the user-separable section 26 is provided with a finger pull tab 32 at its outer end, preferably opposite living hinge 27, to facilitate its separation at the thin-walled border portion 24. In embodiments that do not allow for complete removal of the user-separable section 26, a latching arrangement 33 preferably is provided to permit a user to securely re-cover an opened pen needle with the user-separable section 26 and thus protect against accidental needle sticks. Latching arrangement 33 includes a first latching portion on proximal cover 22 and a second latching portion on finger pull tab 32 configured to engage the first latching portion. In the embodiment shown in FIGS. 3 and 4, the first latching portion is a laterally projecting nose 36 on the periphery or sidewall of proximal cover 22, and the second latching portion is a cooperating facing aperture 38 on pull tab 32 configured to capture the nose 36. Alternatively, the latching mechanism may comprise an inwardly facing nose or rib on pull tab 32 that snaps under the peripheral edge of proximal cover 22; or it may comprise any other suitable mating features on pull tab 32 and proximal cover 22 that enable re-covering of the pen needle and hub by user-separable section 26. Because rupture of the thin-walled border portion 24 is readily discernable, a user can easily tell that the pen needle cover has been opened previously even though the opening of the distal cover is closed.

Molded indicia may be provided on the plastic proximal cover 22, viewable from the exterior of the cover. In preferred embodiments, the indicia are visible even after the user-separable section 26 is separated along tear line 24. For example, the molded indicia may be provided on the outer or inner surface of user-separable section 26 if that section remains connected by a living hinge or other means; or the indicia may be provided on a portion of the proximal cover 22 that remains undisturbed. If the proximal cover 22 is transparent, indicia applied to its inner surface or to the adjacent flange 12 of the distal cover 20 will be readable through the plastic. The indicia may identify the manufacturer of the part, the lot number, or provide other important and potentially useful information.

The foregoing description of the preferred embodiments is not to be deemed limiting of the invention, which is defined by the appended claims. Persons skilled in the art, relying on the foregoing disclosure, may practice variants of the embodiments described without departing from the scope of the invention claimed. Although described in connection with the delivery of self-administered insulin, pen needles packaged as described herein may be used to deliver other liquid medications. Features described or claimed herein in connection with one embodiment may be adapted for use with other embodiments without departing from the scope of the invention.

The invention claimed is:

1. A pen needle outer cover, comprising:
   a plastic distal cover portion having a closed distal end, an opening at a proximal end and an attachment member adjacent the opening; and
   a plastic proximal cover portion engaging the attachment member, the proximal cover portion having a rupturable, thin-walled border portion defining a user-separable section of the proximal cover portion; wherein
   the user-separable section has a finger pull tab at an outer end thereof;
   the distal cover portion includes a first latching portion; and
   the finger pull tab includes a second latching portion configured to engage the first latching portion.

2. The pen needle outer cover according to claim 1, including a living hinge on the proximal cover portion connecting the user-separable section to the proximal cover portion and allowing the user-separable section to pivot when the thin-walled border portion is ruptured.

3. The pen needle outer cover according to claim 2, wherein the living hinge divides the thin-walled border portion into two segments.

4. The pen needle outer cover according to claim 1, wherein the user-separable section can be removed completely from the proximal cover portion.

5. The pen needle outer cover according to claim 4, wherein the thin-walled border portion is continuous, thus defining a closed shape.

6. The pen needle outer cover according to claim 1, wherein the attachment member includes a flange adjacent the opening of the distal cover portion.

7. The pen needle outer cover according to claim 1, wherein the attachment member includes a flange running substantially around the opening of the distal cover portion, and the proximal cover portion is snap-fit over the flange.

8. The pen needle outer cover according to claim 1, wherein the distal cover portion and the proximal cover portion are made of injection molded polyethylene and the thin-walled border portion has a thickness in the range of 0.004 to 0.012 mm.

9. The pen needle outer cover according to claim 1, wherein the first latching portion can be releasably re-engaged with the second latching portion after the user-separable section has been separated at the thin-walled border portion.

10. The pen needle outer cover according to claim 1, wherein a sidewall of the distal cover portion includes the first latching portion.

11. The pen needle outer cover according to claim 1, wherein the first latching portion includes a lateral projection and the second latching portion includes an aperture configured to capture the lateral projection.

12. The pen needle outer cover according to claim 1, wherein the proximal cover portion is transparent.

13. A pen needle assembly, comprising:
   a hub and a cannula fixed axially to the hub; and
   the pen needle outer cover of claim 1.

14. The pen needle assembly according to claim 13, including a living hinge on the proximal cover portion connecting the user-separable section to the proximal cover portion and allowing the user-separable section to pivot when the thin-walled border portion is ruptured.

15. The pen needle assembly according to claim 14, wherein the living hinge divides the thin-walled border portion into two segments.

16. The pen needle assembly according to claim 13, wherein the user-separable section can be removed completely from the proximal cover portion.

17. The pen needle assembly according to claim 16, wherein the thin-walled border portion is continuous, thus defining a closed shape.

* * * * *

UNITED STATES PATENT AND TRADEMARK OFFICE
CERTIFICATE OF CORRECTION

| | | |
|---|---|---|
| PATENT NO. | : 10,398,828 B2 | Page 1 of 1 |
| APPLICATION NO. | : 15/317461 | |
| DATED | : September 3, 2019 | |
| INVENTOR(S) | : Dibiasi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 251 days.

Signed and Sealed this
Second Day of June, 2020

Andrei Iancu
*Director of the United States Patent and Trademark Office*